(12) United States Patent
Brannan (10) Patent No.: US 8,974,449 B2
(45) Date of Patent: Mar. 10, 2015

(54) DUAL ANTENNA ASSEMBLY WITH USER-CONTROLLED PHASE SHIFTING

(75) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 1185 days.

(21) Appl. No.: 12/837,820

(22) Filed: Jul. 16, 2010

(65) Prior Publication Data
US 2012/0016360 A1    Jan. 19, 2012

(51) Int. Cl.
  A61B 18/14    (2006.01)
  A61B 18/18    (2006.01)
  A61N 5/04     (2006.01)
  A61B 18/00    (2006.01)

(52) U.S. Cl.
  CPC ..... *A61B 18/1815* (2013.01); *A61B 2018/0019* (2013.01); *A61B 2018/1861* (2013.01); *A61N 5/045* (2013.01)
  USPC .................. 606/33; 606/41; 607/99; 607/100; 607/101

(58) Field of Classification Search
  USPC ................... 606/41, 33; 607/99–101
  See application file for complete search history.

(56) References Cited

U.S. PATENT DOCUMENTS

| D263,020 | S | 2/1982 | Rau, III |
| 4,448,198 | A * | 5/1984 | Turner ............. 607/99 |
| D295,893 | S | 5/1988 | Sharkany et al. |
| D295,894 | S | 5/1988 | Sharkany et al. |
| 5,057,106 | A * | 10/1991 | Kasevich et al. ........... 606/33 |
| 5,767,756 | A | 6/1998 | Hwang |
| 5,769,879 | A | 6/1998 | Richard |
| D424,694 | S | 5/2000 | Tetzlaff et al. |
| D425,201 | S | 5/2000 | Tetzlaff et al. |
| 6,061,551 | A | 5/2000 | Sorrells et al. |
| 6,208,903 | B1 * | 3/2001 | Richards et al. ........... 607/101 |
| 6,228,079 | B1 | 5/2001 | Koenig |
| D449,886 | S | 10/2001 | Tetzlaff et al. |
| D457,958 | S | 5/2002 | Dycus et al. |
| D457,959 | S | 5/2002 | Tetzlaff et al. |
| 6,477,426 | B1 | 11/2002 | Fenn et al. |
| 6,788,977 | B2 | 9/2004 | Fenn et al. |

(Continued)

FOREIGN PATENT DOCUMENTS

CN    1103807    6/1995
DE    390937     3/1924

(Continued)

OTHER PUBLICATIONS

U.S. Appl. No. 08/483,742, filed Jun. 7, 1995.

(Continued)

*Primary Examiner* — William Thomson
*Assistant Examiner* — Victor Shapiro (57) ABSTRACT

An electrosurgical ablation system includes an energy source adapted to supply energy to an energy delivery device. The energy delivery device includes a handle assembly configured to couple a pair of antennas extending from a distal end thereof to the energy source for application of energy to tissue. A power splitting device is operatively associated with the handle assembly and has an input adapted to connect to the energy source and a pair of output channels operably coupled to the respective pair of antennas. A phase shifter is operatively associated with the handle assembly and is operably coupled to the pair of output channels. The phase shifter is configured to selectively shift a phase relationship between the pair of output channels.

19 Claims, 4 Drawing Sheets

(56) References Cited

U.S. PATENT DOCUMENTS

| | | | |
|---|---|---|---|
| D496,997 S | 10/2004 | Dycus et al. | |
| D499,181 S | 11/2004 | Dycus et al. | |
| D525,361 S | 7/2006 | Hushka | |
| 7,113,832 B2* | 9/2006 | Longo | 607/101 |
| D531,311 S | 10/2006 | Guerra et al. | |
| D533,942 S | 12/2006 | Kerr et al. | |
| D535,027 S | 1/2007 | James et al. | |
| 7,160,292 B2* | 1/2007 | Moorman et al. | 606/33 |
| D541,418 S | 4/2007 | Schechter et al. | |
| D541,938 S | 5/2007 | Kerr et al | |
| D564,662 S | 3/2008 | Moses et al. | |
| D613,412 S | 4/2010 | DeCarlo | |
| 2003/0153908 A1* | 8/2003 | Goble et al. | 606/41 |
| 2004/0044385 A1* | 3/2004 | Fenn et al. | 607/100 |
| 2007/0049917 A1 | 3/2007 | Yang et al. | |
| 2007/0118193 A1* | 5/2007 | Turner et al. | 607/101 |
| 2007/0191827 A1* | 8/2007 | Lischinsky et al. | 606/34 |
| 2008/0033426 A1* | 2/2008 | Machell | 606/41 |
| 2010/0030206 A1 | 2/2010 | Brannan | |
| 2010/0030210 A1 | 2/2010 | Paulus | |
| 2010/0036369 A1 | 2/2010 | Hancock | |
| 2010/0087808 A1 | 4/2010 | Paulus | |
| 2010/0114086 A1 | 5/2010 | Deem | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 2149343 | 2/2010 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 9309845 | 5/1993 |
| WO | WO 2008068485 | 6/2008 |
| WO | WO 2009075904 | 6/2009 |
| WO | WO2010/035831 | 4/2010 |

OTHER PUBLICATIONS

U.S. Appl. No. 08/136,098, filed Oct. 14, 1993.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/423,609, filed Apr. 14, 2009.
U.S. Appl. No. 12/436,231, filed May 6, 2009.
U.S. Appl. No. 12/436,237, filed May 6, 2009.
U.S. Appl. No. 12/436,239, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/556,238, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.

(56) References Cited

OTHER PUBLICATIONS

U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,323, filed Nov. 16, 2009.
U.S. Appl. No. 12/619,462, filed Nov. 16, 2009.
U.S. Appl. No. 12/620,289, filed Nov. 17, 2009.
U.S. Appl. No. 12/642,623, filed Dec. 18, 2009.
U.S. Appl. No. 12/686,726, filed Jan. 13, 2010.
U.S. Appl. No. 12/692,856, filed Jan. 25, 2010.
U.S. Appl. No. 12/696,671, filed Jan. 29, 2010.
U.S. Appl. No. 12/696,966, filed Jan. 29, 2010.
U.S. Appl. No. 12/701,030, filed Feb. 5, 2010.
U.S. Appl. No. 12/708,974, filed Feb. 19, 2010.
U.S. Appl. No. 12/709,014, filed Feb. 19, 2010.
U.S. Appl. No. 12/712,864, filed Feb. 25, 2010.
U.S. Appl. No. 12/713,429, filed Feb. 26, 2010.
U.S. Appl. No. 12/713,515, filed Feb. 26, 2010.
U.S. Appl. No. 12/713,641, filed Feb. 26, 2010.
U.S. Appl. No. 12/722,034, filed Mar. 11, 2010.
U.S. Appl. No. 12/731,367, filed Mar. 25, 2010.
U.S. Appl. No. 12/732,508, filed Mar. 26, 2010.
U.S. Appl. No. 12/732,521, filed Mar. 26, 2010.
U.S. Appl. No. 12/761,267, filed Apr. 15, 2010.
U.S. Appl. No. 12/769,457, filed Apr. 28, 2010.
U.S. Appl. No. 12/772,675, filed May 3, 2010.
U.S. Appl. No. 12/777,984, filed May 11, 2010.
U.S. Appl. No. 12/786,671, filed May 25, 2010.
U.S. Appl. No. 12/787,639, filed May 26, 2010.
U.S. Appl. No. 12/792,904, filed Jun. 3, 2010.
U.S. Appl. No. 12/792,932, filed Jun. 3, 2010.
U.S. Appl. No. 12/792,947, filed Jun. 3, 2010.
U.S. Appl. No. 12/792,970, filed Jun. 3, 2010.
U.S. Appl. No. 12/793,037, filed Jun. 3, 2010.
U.S. Appl. No. 12/819,330, filed Jun. 21, 2010.
U.S. Appl. No. 12/823,211, filed Jun. 25, 2010.
U.S. Appl. No. 12/826,902, filed Jun. 30, 2010.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman et al., "Laparoscopic Intestinal Resection With the LigaSure™ Vessel Sealing System: A Case Report" Innovations That Work, Feb. 2002.

(56) References Cited

OTHER PUBLICATIONS

Humphries Jr. et al., "Finite-Element Codes to Model Electrical Heating and Non•LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.

(56) References Cited

OTHER PUBLICATIONS

Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.

(56) References Cited

OTHER PUBLICATIONS

European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report for European Application No: 11005827.8 dated Nov. 1, 2011.
Japanese Office Action, Application No. 2011-156313 dated Nov. 18, 2014.
Published Japanese Translation No. 9-501333 of the PCT International Application.
Japanese Patent Application Laid-Open No. 2008-21493.

* cited by examiner

DUAL ANTENNA ASSEMBLY WITH USER-CONTROLLED PHASE SHIFTING

BACKGROUND

1. Technical Field

The present disclosure relates to apparatus and methods for providing energy to tissue and, more particularly, to devices and electromagnetic radiation delivery procedures utilizing ablation probes and methods of controlling the delivery of electromagnetic radiation to tissue.

2. Discussion of Related Art

Treatment of certain diseases requires destruction of malignant tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of cancer cells have been found to denature at elevated temperatures that are slightly lower than temperatures normally injurious to healthy cells. Known treatment methods, such as hyperthermia therapy, use electromagnetic radiation to heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator, which functions as an energy source, and a microwave surgical instrument having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

Microwave energy is typically applied via antenna assemblies that can penetrate tissue. Several types of antenna assemblies are known, such as monopole and dipole antenna assemblies. In monopole and dipole antenna assemblies, microwave energy generally radiates perpendicularly away from the axis of the conductor. A monopole antenna assembly includes a single, elongated conductor that transmits microwave energy. A typical dipole antenna assembly has two elongated conductors, which are linearly aligned and positioned end-to-end relative to one another with an electrical insulator placed therebetween. Each conductor may be about ¼ of the length of a wavelength of the microwave energy, making the aggregate length of the two conductors about ½ of the wavelength of the supplied microwave energy. During certain procedures, it can be difficult to assess the extent to which the microwave energy will radiate into the surrounding tissue, making it difficult to determine the area or volume of surrounding tissue that will be ablated.

SUMMARY

According to an embodiment of the present disclosure, an electrosurgical ablation system includes an energy source adapted to supply energy to an energy delivery device. The energy delivery device includes a handle assembly configured to couple a pair of antennas extending from a distal end thereof to the energy source for application of energy to tissue. A power splitting device is operatively associated with the handle assembly and has an input adapted to connect to the energy source and a pair of output channels operably coupled to the respective pair of antennas. A phase shifter is operatively associated with the handle assembly and is operably coupled to the pair of output channels. The phase shifter is configured to selectively shift a phase relationship between the pair of output channels.

According to another embodiment of the present disclosure, a method of providing energy to a target tissue includes the steps of positioning an energy delivery device relative to a target tissue site and equally dividing energy supplied to the energy delivery device from an energy source between a pair of channels in a predetermined phase relationship. The method also includes selectively shifting the phase relationship between the pair of channels and applying the equally divided energy to the target tissue in the selectively adjusted phase relationship.

According to another embodiment of the present disclosure, a method of providing energy to a target tissue includes the steps of positioning a microwave antenna assembly relative to a target tissue site and equally dividing energy supplied to the microwave antenna assembly from an energy source between a pair of channels in a predetermined phase relationship. The method also includes the step of selectively shifting the phase of at least one channel +/−90 degrees to shift the phase relationship between the channels to one of an in-phase configuration and an out-of-phase configuration based on a desired tissue ablation geometry. The method also includes the step of applying the equally divided energy from the pair of channels to a corresponding pair of antennas for application to target tissue.

DETAILED DESCRIPTION

Hereinafter, embodiments of the presently disclosed tissue ablation systems are described with reference to the accompanying drawings. Like reference numerals may refer to similar or identical elements throughout the description of the figures. As used herein, the term "microwave" generally refers to electromagnetic waves in the frequency range of 300 megahertz (MHz) (3×108 cycles/second) to 300 gigahertz (GHz) (3×1011 cycles/second). As used herein, the phrase "transmission line" generally refers to any transmission medium that can be used for the propagation of signals from one point to another.

Various embodiments of the present disclosure provide electrosurgical systems for treating tissue and methods of controlling the delivery of electromagnetic radiation to tissue. Embodiments may be implemented using electromagnetic radiation at microwave frequencies or at other frequencies. Electrosurgical systems for treating tissue, according to various embodiments of the present disclosure, deliver microwave power to an electrosurgical device. An electrosurgical device, such as an ablation antenna, for implementing embodiments of the present disclosure may be inserted directly into tissue, inserted through a lumen, such as a vein, needle or catheter, placed into the body during surgery by a clinician, or positioned in the body by other suitable methods known in the art.

The present disclosure relates generally to an ablation system that equally splits microwave power between a pair of antennas of an ablation device at a predetermined phase relationship. The phase relationship is user-selected and is based on an ablation procedure being performed and/or on a desired ablation pattern or geometry. As discussed in further detail below, by controlling the phase of ablation antennas with respect to each other, according to embodiments of the present disclosure, a desired effect on tissue between the antennas is produced.

Figure 1:
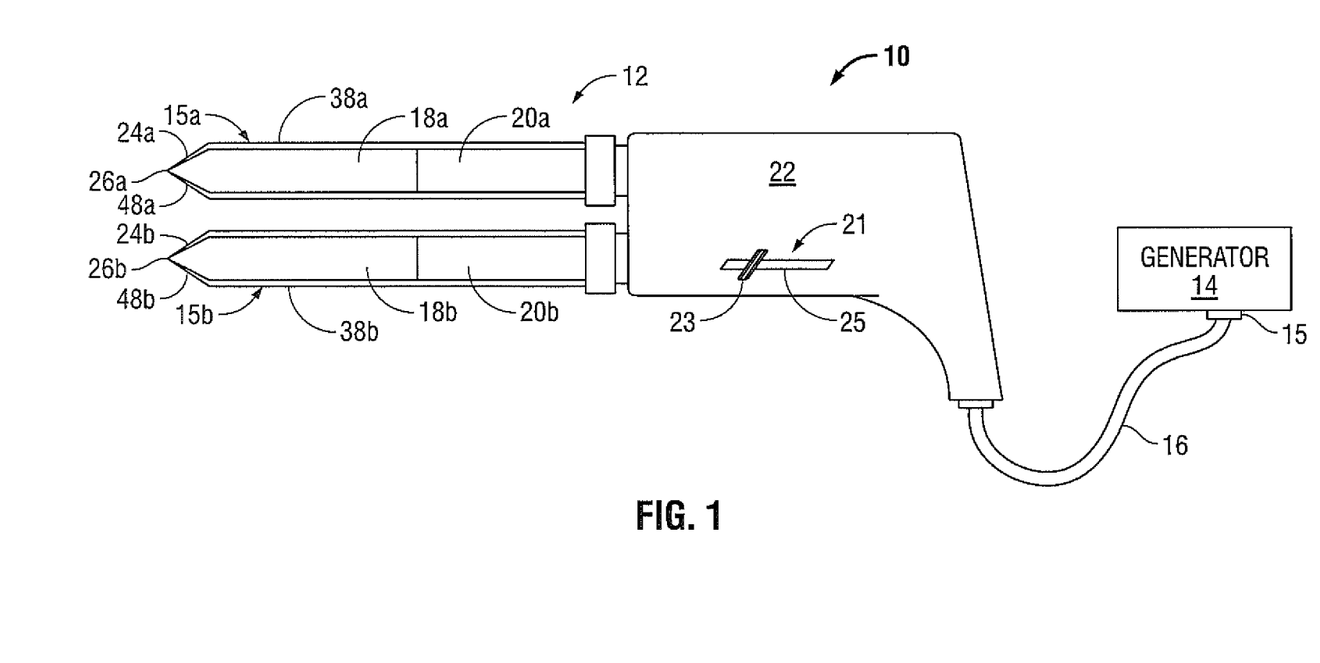
FIG. 1 is a schematic diagram of an electrosurgical system for treating tissue, according to an embodiment of the present disclosure.

FIG. 1 shows an ablation system 10 that includes an antenna assembly 12 coupled to an output 15 of an electrosurgical generator 14 via a flexible coaxial cable 16. The generator 14 is adapted to provide microwave energy at an operational frequency from about 300 MHz to about 6000 MHz, although other suitable frequencies (e.g., radio frequency) are also contemplated.

Figure 2A:
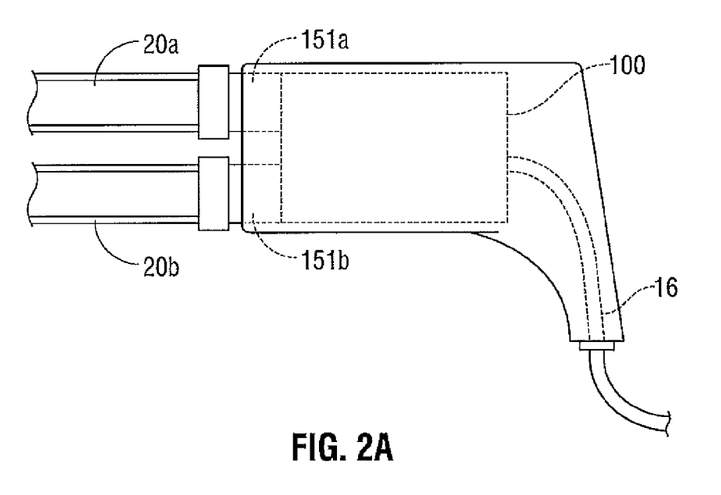
FIG. 2A is a partial schematic diagram of the electrosurgical system of FIG. 1 showing a control circuit in accordance with an embodiment of the present disclosure.

In the illustrated embodiment, the antenna assembly 12 includes a pair of antennas 15a and 15b disposed substantially parallel to each other, for example, spaced about 5 millimeters (mm) apart. Antennas 15a, 15b are inserted directly into tissue or placed into the body during surgery by a clinician, or positioned in the body by other suitable methods. Antennas 15a, 15b include radiating portions 18a, 18b, respectively, that are connected by respective feedlines 20a, 20b, to the cable 16. More specifically, the antenna assembly 12 is coupled to the cable 16 through a connection hub or handle 22 that is connected in fluid communication with sheaths 38a, 38b that enclose radiating portions 18a, 18b and feedlines 20a, 20b, respectively. As shown schematically in FIG. 2A and as discussed in further detail below with respect to FIG. 2B, a control circuit 100 disposed within handle 22 is configured to connect to output 15 of generator 14 and equally split energy supplied by generator 14 between a pair of channels 151a and 151b in a predetermined phase relationship to drive antennas 15a and 15b, respectively. Channels 151a, 151b electrically connect to a variable phase shifter 180 disposed within control circuit 100. Phase shifter 180 is operably coupled to a user-accessible switching mechanism 21 disposed on the handle 22 that allows the user to selectively shift the phase of either channel 151a and/or 151b relative to the other channel to achieve a desired phase relationship (e.g., in-phase, out-of-phase) between antennas 15a, 15b, as discussed in detail below.

As shown in the illustrated embodiment of FIG. 1, switching mechanism 21 includes a slide button 23 that is disposed about the exterior of the handle 22 and is configured to slide within a groove 25 defined at least partially through the handle 22 to control the phase relationship between channels 151a, 151b in mutual cooperation with variable phase shifter 180. More specifically, variable phase shifter 180 may include an electrical transmission line such as microstrip (not shown) that is suitably positioned within handle 22 relative to groove 25 to be mechanically engaged by slide button 23 for controlling the variable phase shifter 180. For purposes of connecting to and controlling variable phase shifter 180 from the exterior of handle 22, switching mechanism 21 may, in lieu of slide button 23, include any suitable switching mechanism such as, for example without limitation, a toggle switch, a push button, a dial, a potentiometer, an air-gap switch, a paddle actuator, a lever, or the like.

Channels 151a and/or 151b are electrically connected, via corresponding outputs 101a and 101b of variable phase shifter 180, to feedlines 20a and 20b, respectively, to supply electrosurgical energy to radiating portions 18a, 18b for application to tissue. The sheaths 38a, 38b enclose radiating portions 18a, 18b, respectively, and feedlines 20a, 20b to form a chamber (not shown) that allows one or more materials such as, for example, fluid, gas, coolant, chemicals, saline, water, powdered solids, or any combination thereof, to circulate within and/or occupy space within the chamber. In some embodiments, handle 22 may be coupled to a suitable supply pump (not shown) adapted to supply fluid or coolant to the chamber. In some embodiments, antenna assembly 12 may be embodied as, for example without limitation, a radiofrequency monopolar and/or bipolar electrode assembly, an ultrasound transducer, laser fiber, a direct current (DC) heating element, or the like.

Antenna assembly 12 also includes a tip 48a, 48b disposed at a distal end of each radiating portion 18a, 18b, respectively. Each tip 48a, 48b has a respective tapered end 24a, 24b that terminates, in some embodiments, at a respective pointed end 26a, 26b to allow for insertion into tissue with minimal resistance. In those cases where the radiating portions 18a, 18b are inserted into a pre-existing opening, tips 48a, 48b may be rounded or flat. Tips 48a, 48b may be formed from a variety of heat-resistant materials suitable for penetrating tissue, such as metals (e.g., stainless steel) and various thermoplastic materials, such as polyetherimide, and polyamide thermoplastic resins.

In embodiments, the antenna assembly 12 is a microwave antenna configured to allow direct insertion or penetration into tissue of a patient. The antenna assembly 12 may be axially rigid to allow for tissue penetration. The antenna assembly 12 is sufficiently small in diameter to be minimally invasive of the body, which may reduce the preparation of the patient as might be required for more invasive penetration of the body. The antenna assembly 12 is inserted directly into tissue, inserted through a lumen (e.g., a vein, a needle, a catheter), placed into the body during surgery by a clinician, or positioned in the body by other suitable methods.

Figure 2B:
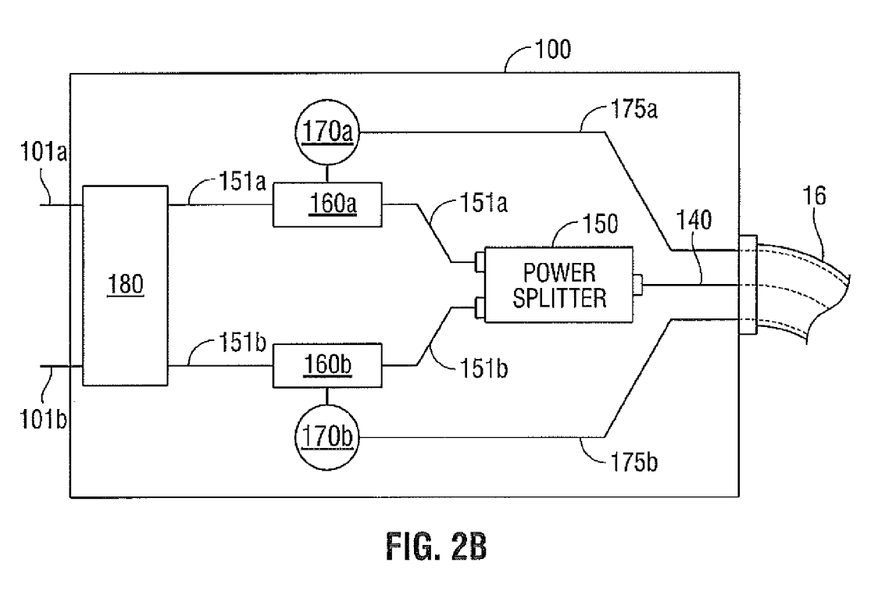
FIG. 2B is a schematic diagram of the control circuit of FIG. 2A.

FIG. 2B is a schematic diagram of control circuit 100, according to one embodiment of the present disclosure. Control circuit 100 includes a power splitter 150 that is electrically connected via a transmission line 140 to the output 15 of generator 14. The power splitter 150 may be implemented by any suitable power divider that provides an equal or unequal power split at its output ports while substantially maintaining a predetermined phase relationship. For example, the power splitter 150 may be implemented using a 2-way power divider that provides an equal power split at its output ports while maintaining a phase difference of +/−90 degrees (e.g., via a 90 degree power divider IC).

Power splitter 150 receives, as an input signal, electrosurgical output from the generator 14. The power splitter 150 splits the input signal received from generator 14 equally between a pair of channels 151a and 151b at a phase difference of 90 degrees. Channels 151a and 151b pass through a pair of corresponding directional couplers 160a and 160b that are configured to couple reflected power on channels 151a, 151b to corresponding rectifiers 170a, 170b (e.g., microwave to DC rectifiers) for purposes of reflected power monitoring. Transmission lines 175a and 175b electrically connect rectifiers 170a, 170b, respectively, to generator 14 by way of cable 16 such that rectifiers 170a, 170b may communicate data to generator 14 for processing.

When coupling electromagnetic radiation such as microwaves from a source to an applicator, in order to maximize the amount of energy transferred from the source (e.g., generator 14) to the load (e.g., antennas 15a, 15b), the line and load impedances should match. If the line and load impedances do not match (e.g., an impedance mismatch) a reflected wave may be created that can generate a standing wave, which contributes to a power loss associated with the impedance mismatch. In embodiments, the generator 14 is configured to control energy output to the antenna assembly 12 based on an outer feedback loop that monitors a reflectance parameter (e.g., received from rectifier(s) 175a and/or 175b) such as a mismatch detected between the load impedance and the line impedance. Such an impedance mismatch may cause a portion of the power, so called "reflected power," from the generator 14 to not reach the tissue site and cause the power delivered, the so called "forward power", to vary in an irregular or inconsistent manner. It is possible to determine ablation completeness based on the impedance mismatch by measuring and analyzing the reflected and forward power. In particular, the generator 14 measures energy delivery properties, namely the reflected power, to determine ablation completeness. When the reflected power detected reaches a particular or predetermined level indicative of ablation completeness or reaches a particular or predetermined rate of change over time indicative of ablation completeness, the generator 14 terminates or adjusts energy output and alerts the user of the ablation completeness via an audible and/or visual indicator (not shown) disposed on the antenna assembly 12 and/or the generator 14.

Channels 151a, 151b pass through variable phase shifter 180 that, as described above, is user-controlled via the switching mechanism 23 disposed on handle 22. At this juncture (e.g., prior to passing through variable phase shifter 180), channels 151a, 151b are 90 degrees out-of-phase, as discussed hereinabove.

Figure 3A:
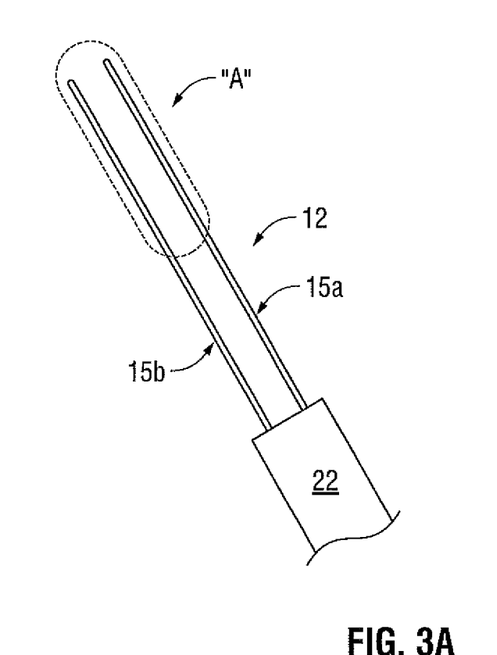
FIGS. 3A and 3B are schematic diagrams of antennas assemblies illustrating tissue ablation geometries in accordance with various embodiments of the present disclosure.
Figure 3B:
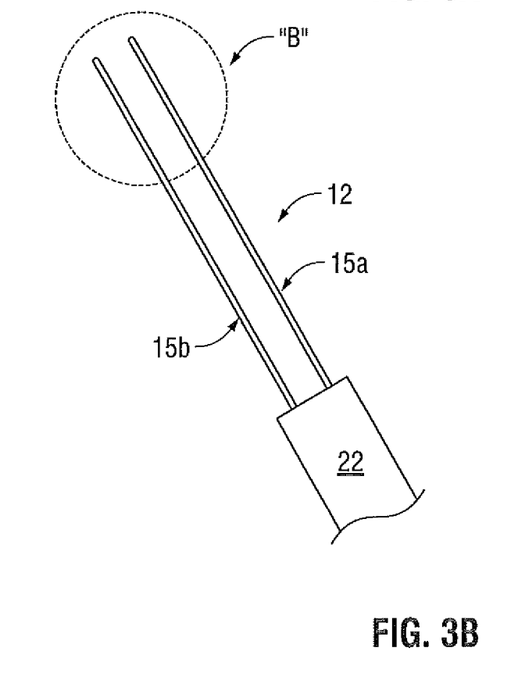

Referring for a moment to FIGS. 3A and 3B, by controlling the phase of antennas 15a, 15b with respect to each other, according to embodiments of the present disclosure, a desired effect on tissue between the antennas 15a, 15b is produced. In a resection procedure where a long thin ablation pattern is desired, depicted in phantom and referenced as "A" in FIG. 3A, a 180 degree out-of-phase relationship between antennas 15a, 15b produces a desired effect on tissue. More specifically, the out-of-phase relationship between antennas 15a, 15b generates proximal energy propagation therebetween to produce the elongated ablation pattern "A" suitable for planar tissue coagulation. In an ablation procedure where a generally spherical ablation pattern with a relatively larger radius is desired, depicted in phantom and referenced as "B" in FIG. 3B, an in-phase relationship between antennas 15a, 15b produces a desired effect on tissue. More specifically, the in-phase relationship between antennas 15a, 15b substantially eliminates proximal energy propagation therebetween to produce a generally spherical ablation pattern "B" suitable for focal tissue ablation proximate radiating portions 18a, 18b of antennas 15a, 15b, respectively.

As mentioned above, variable phase shifter 180 is user-controlled via switching mechanism 23 disposed on handle 22 such that channels 151a, 151b may be configured in various phase relationships relative to one another in accordance with a desired tissue ablation pattern or geometry, as described above. For example, phase shifter 180 may include an out-of-phase configuration wherein the phase of one of channels 151a or 151b is shifted 90 degrees such that channels 151a, 151b are changed from being 90 degrees out-of-phase (via the power splitter 150) to being 180 degrees out-of-phase. As described hereinabove, the 180 degree out-of-phase relationship between channels 151a, 151b produces a long thin ablation pattern "A" that is ideal for a tissue resection procedure. In this manner, when channels 151a, 151b are 180 degrees out-of-phase, antenna assembly 12 is said to be operating in a "tissue resection mode".

Phase shifter 180 may also include, by way of example, an in-phase configuration wherein the phase of one of channels 151a or 151b is shifted 90 degrees such that channels 151a, 151b are changed from being 90 degrees out-of-phase (via the power splitter 150) to being in-phase or having a 0 degree phase difference. As described hereinabove, the in-phase relationship between channels 151a, 151b produces a generally spherical ablation pattern "B" with a relatively larger radius that is ideal for a tissue ablation procedure. In this manner, when channels 151a, 151b are in-phase, antenna assembly 12 is said to be operating in a "tissue ablation mode".

Figure 4:
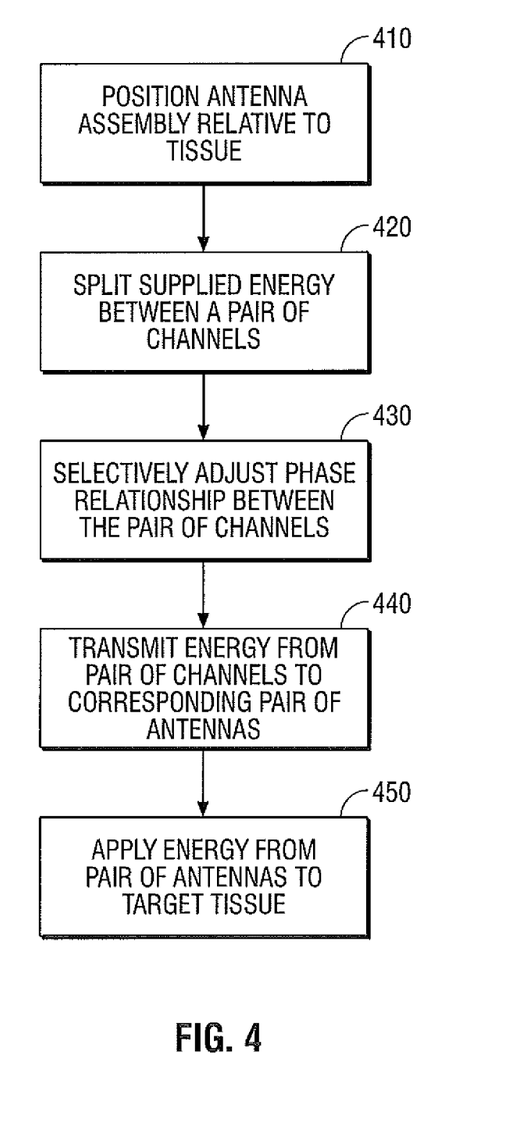
FIG. 4 is a block diagram illustrating a method for treating tissue, according to an embodiment of the present disclosure.

FIG. 4 is a flowchart illustrating a method for providing energy to a target tissue, according to an embodiment of the present disclosure. Referring initially to step 410, antennas 15a, 15b of antenna assembly 12 are positioned relative to the target tissue. The antenna assembly 12 is inserted directly into tissue, inserted through a lumen (e.g., a vein, needle, or catheter), placed into the body during surgery by a clinician, or positioned in the body by other suitable methods.

In step 420, microwave power is supplied by generator 14 to the antenna assembly 12 and is split equally between a pair of channels 151a, 151b by the power splitter 150 in a predetermined phase relationship (e.g., +/−90 degrees).

In step 430, the phase relationship between channels 151a, 151b is selectively adjusted through use of a user-controlled variable phase shifter 180 in accordance with a desired ablation pattern (e.g., pattern "A" or pattern "B"), a desired phase configuration (e.g., in-phase, out-of-phase), a desired phase relationship (e.g., +/−0 degrees, +/−90 degrees, +/−180 degrees, etc.), and/or a desired mode of operation of antenna assembly 12 (e.g., tissue resection mode, tissue ablation mode).

In step 440, the microwave power is selectively transmitted from channels 151a, 151b to radiating portions 18a, 18b, respectively, via corresponding outputs 101a, 101b of the variable phase shifter 180.

In step 450, microwave energy from radiating portions 18a, 18b is applied to the target tissue to achieve the desired ablation pattern or geometry.

In some embodiments, the method for providing energy to a target tissue includes the step of monitoring reflected power detected on channels 151a, 151b, as described hereinabove in connection with FIG. 213, and controlling energy supplied to the antenna assembly 12 by generator 14 based on the detected reflected power.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical ablation system, comprising:
an energy source adapted to supply energy to an energy delivery device, the energy delivery device including a handle assembly configured to couple a pair of antennas configured for insertion through tissue and extending from a distal end thereof to the energy source for application of energy to tissue;
a power splitting device disposed within the handle assembly and having an input adapted to connect to the energy source and a pair of output channels operably coupled to the respective pair of antennas; and
a phase shifter operatively associated with the handle assembly and operably coupled to the pair of output channels, the phase shifter configured to selectively shift a phase relationship between the pair of output channels.

2. An electrosurgical ablation system according to claim 1, wherein the energy source is a microwave generator adapted to supply microwave energy to the energy delivery device.

3. An electrosurgical ablation system according to claim 1, further comprising at least one rectifier disposed in operative communication with the energy source, the at least one rectifier configured to monitor reflected power detected on the pair of output channels, wherein the energy source controls the energy supplied to the energy delivery device based on the detected reflected power.

4. An electrosurgical ablation system according to claim 1, wherein the phase shifter is user-controlled via a switch assembly disposed on the handle assembly and operably coupled to the phase shifter.

5. An electrosurgical ablation system according to claim 4, wherein the switch assembly includes a slide switch accessible from an exterior of the handle assembly and configured to slide within a groove defined within the handle assembly to control the phase shifter.

6. An electrosurgical ablation system according to claim 1, wherein the phase shifter is selectively controlled to generate a phase difference of +/−180 degrees between the pair of antennas.

7. An electrosurgical ablation system according to claim 6, wherein the energy delivery device is configured to operate in a tissue resection mode when the phase difference between the pair of antennas is +/−180 degrees.

8. An electrosurgical ablation system according to claim 1, wherein the phase shifter is selectively controlled to generate an in-phase relationship between the pair of antennas.

9. An electrosurgical ablation system according to claim 8, wherein the energy delivery device is configured to operate in a tissue ablation mode when an in-phase relationship exists between the pair of antennas.

10. An electrosurgical ablation system according to claim 1, wherein the phase shifter is selectively controlled to generate an in-phase relationship between the pair of antennas to produce a generally spherical ablation geometry proximate a radiating portion of each of the pair of antennas.

11. An electrosurgical ablation system according to claim 1, wherein the phase shifter is selectively controlled to generate an out-of-phase relationship between the pair of antennas to produce a generally elongated ablation geometry proximate a radiating portion of each of the pair of antennas.

12. An electrosurgical ablation system according to claim 1, wherein the pair of antennas are substantially parallel to one another.

13. An electrosurgical ablation system according to claim 1, wherein the power splitting device generates a substantially equal power split between the pair of output channels while maintaining a phase difference of +/−90 degrees between the pair of output channels.

14. A method of providing energy to a target tissue, the method comprising:
inserting an energy delivery device into a target tissue site, the energy delivery device including:
a handle assembly configured to couple a pair of antennas configured for insertion through tissue and extending from a distal end thereof;
a power splitting device disposed within the handle assembly and having an input adapted to connect to an energy source and a pair of output channels operably coupled to the respective pair of antennas; and
a phase shifter operatively associated with the handle assembly and operably coupled to the pair of output channels, the phase shifter configured to selectively shift a phase relationship between the pair of output channels;
using the power splitting device to equally divide energy between the pair of channels in a predetermined phase relationship;
selectively shifting the phase relationship between the pair of channels; and applying the equally divided energy to the target tissue in the selectively adjusted phase relationship.

15. A method according to claim 14, wherein selectively shifting includes selectively shifting the phase relationship between an in-phase configuration and an out-of-phase configuration based on a desired ablation geometry.

16. A method according to claim 15, wherein selectively shifting includes shifting the phase of one of the channels +/−90 degrees to shift the phase relationship to the in-phase configuration and shifting the phase of the other channel +/−90 degrees to shift the phase relationship to the out-of-phase configuration.

17. A method according to claim 14, wherein the predetermined phase relationship of the equally dividing step is a phase difference of +/−90 degrees between the pair of channels.

18. A method according to claim 14, wherein selectively shifting includes sliding a switch relative to the energy delivery device to selectively shift the phase relationship between the channels.

19. A method of providing energy to a target tissue, the method comprising:
inserting a microwave antenna assembly through tissue and into a target tissue site;
using a power splitting device disposed within the microwave antenna assembly to equally divide energy between a pair of channels in a predetermined phase relationship;
selectively shifting the phase of at least one channel +/−90 degrees to shift the phase relationship between the channels to one of an in-phase configuration and an out-of-phase configuration based on a desired tissue ablation geometry; and
applying the equally divided energy from the pair of channels to a corresponding pair of antennas for application to target tissue.

* * * * *